US012725705B2

(12) United States Patent
Segaram et al.

(10) Patent No.: US 12,725,705 B2
(45) Date of Patent: Sep. 1, 2026

(54) MOBILE TREATMENT SYSTEM FOR DRY EYE SYNDROME

(71) Applicant: TeleMedC LLC, Fremont, CA (US)

(72) Inventors: Para K. Segaram, Campbell, CA (US); Di Xiao, Brisband (AU); Daniel Francis Min Yi Yap, Singapore (SG)

(73) Assignee: TeleMedC LLC, Fremont (CO)

( * ) Notice: Subject to any disclaimer, the term of this patent is extended or adjusted under 35 U.S.C. 154(b) by 584 days.

(21) Appl. No.: 18/298,827

(22) Filed: Apr. 11, 2023

(65) Prior Publication Data

US 2023/0326602 A1 Oct. 12, 2023

Related U.S. Application Data

(60) Provisional application No. 63/495,411, filed on Apr. 11, 2023, provisional application No. 63/372,842, filed on Apr. 11, 2022.

(51) Int. Cl.

| | |
|---|---|
| ***G16H 50/20*** | (2018.01) |
| ***A61B 3/00*** | (2006.01) |
| ***A61B 3/14*** | (2006.01) |

(52) U.S. Cl.
CPC ........... *G16H 50/20* (2018.01); *A61B 3/0008* (2013.01); *A61B 3/145* (2013.01); *G06T 2207/30041* (2013.01)

(58) Field of Classification Search
CPC ...... G16H 50/20; A61B 3/0008; A61B 3/145; G06T 2207/30041
USPC .......................................................... 351/206
See application file for complete search history.

(56) References Cited

U.S. PATENT DOCUMENTS

| | | | | |
|---|---|---|---|---|
| 2013/0083185 | A1* | 4/2013 | Coleman, III | A61B 3/14 348/78 |
| 2013/0169933 | A1* | 7/2013 | Wang | A61B 3/14 351/221 |
| 2014/0300862 | A1* | 10/2014 | Perez | A61B 3/102 351/246 |
| 2018/0092534 | A1* | 4/2018 | Nabhan | G16H 30/20 |
| 2019/0209006 | A1* | 7/2019 | Abou Shousha | A61B 3/103 |
| 2020/0060539 | A1* | 2/2020 | Korb | A61B 3/0058 |
| 2020/0081256 | A1* | 3/2020 | Samec | A61B 3/1015 |
| 2020/0163548 | A1* | 5/2020 | Fukuma | A61B 3/145 |
| 2020/0221947 | A1* | 7/2020 | Mino | A61B 3/0025 |
| 2020/0409159 | A1* | 12/2020 | Samec | A61B 3/0008 |

(Continued)

*Primary Examiner* — Sharrief I Broome
(74) *Attorney, Agent, or Firm* — Martensen IP; Michael C. Martensen

(57) ABSTRACT

Disclosed are devices and systems for treating dry eye syndrome by recording and analyzing video of the anterior eye surface through the use of an illuminator device operating with a computer running a software application. The illuminator includes a projector for projecting a simplified Placido ring pattern onto the eye, and an eye cup for aligning the illuminator with the eye. Some embodiments of the illuminator include an onboard camera while other embodiments use the camera system included with a mobile computer such as a smartphone. Also disclosed are methods to use an illuminator and a software application running on a computer to record videos of the anterior eye surface, to perform digital image processing on the videos, and to use the processed images to determine one or more dry eye-related parameters.

10 Claims, 16 Drawing Sheets

(56) References Cited

U.S. PATENT DOCUMENTS

2021/0169321 A1* 6/2021 Fink .................... A61B 3/0008
2021/0257099 A1* 8/2021 Seriani ................ A61B 3/0033

* cited by examiner 12
530
540
534
538
516
514
510
500
550
560
518

MOBILE TREATMENT SYSTEM FOR DRY EYE SYNDROME

CROSS-REFERENCE TO RELATED APPLICATIONS

The present application claims priority to U.S. Provisional Application Ser. No. 63/372,842, filed 11 Apr. 2022 and U.S. Provisional Application Ser. No. 63/495,411, filed 11 Apr. 2023, both of which are hereby incorporated by reference in their entirety for all purposes as if fully set forth herein.

BACKGROUND

Field of the Invention

The disclosed invention relates to devices, systems, and methods for treating dry eye syndrome by recording and analyzing video of the anterior eye through the use of an illumination device with attached mobile computer, wherein the recordings can include an overlaid simplified Placido ring pattern. Also disclosed are methods to use the recorded videos to measure and analyze dry eye-related parameters, to perform dry eye condition monitoring, and to provide dry eye disease self-treatment guidance.

Relevant Background

Dry eye syndrome (DES) is a prevalent condition among all adults. Based on data from the National Health and Wellness Survey, 6.8 percent of the United States adult population (approximately 16.4 million people) have been diagnosed with dry eye syndrome (Farrand, K. F., et al., Am. J. Ophthalmol. 2017; 182:90.). DES affects middle-aged and older adults, contact lens wearers, computer users, gamers, and people living and/or working in dry environments. There is no cure for DES, but symptoms can be relieved with proper diagnosis and treatment.

DES occurs when the eyes do not produce enough tears, or when tears evaporate too quickly or are obstructed from the surface of the eye. Current methods to diagnose DES involve measurements of the following: tear film break-up time, tear film thickness, lipid layer thickness, and/or water sample layer thickness, as well as performing tests, such as a symptom assessment questionnaire, a fluorescein staining test, a Schirmer test, or other appropriate test.

There are a number of devices in the art for diagnosing and monitoring DES that use corneal topography measurement methods, which typically illuminate the eye with a set of concentric lighted rings, known as a Placido Ring or keratoscope pattern. Corneal topography began as a means of treatment for astigmatism and other eye irregularities affecting the topography or shape of the cornea. Such devices are often repurposed to treat DES, and commonly include desktop cameras such as KOWA DR-1α from Kowa Company Ltd, OCULUS Keratograph® 5M from Oculus Inc., and E300 Corneal Topographer from K+Medmont.

A subset of corneal topography devices is designed specifically for DES treatment, for example, TEARSCIENCE LIPIVIEW™ II from Johnson & Johnson. There are several patents or patent applications that disclose such devices, which include, for example, U.S. Pat. No. 10,980,413, which discloses a device and accompanying method for diagnosing, measuring, or analyzing DES, and discusses the ability to determine tear film break-up time and to detect lid margin contact and blink rates. Similarly, U.S. Pat. No. 8,888,286 discloses a DES-specific device capable of measuring the tear film layer thickness of the ocular tear film, a lipid layer thickness, and an aqueous layer thickness on the ocular surface. Another DES-specific device is disclosed in U.S. Pat. No. 8,591,033, wherein the device is capable of measuring the relative thickness of the lipid layer of the precorneal tear film after it is disturbed by blinking. Japan Pat. No. JP2010273800A discloses a DES device and method for measuring an individual's blinking action. Finally, WIPO Application No. WO2015073664A2 discloses a device and accompanying method for diagnosing, measuring, or analyzing DES, to include the detection of eyelid margin contact and blink rates. Additionally, portable corneal topography measurement devices for medical professionals are in use, such as EasyTear® View+ from EasyTear, and Tearscope from Keeler. These devices can be attached to a split lamp to provide illumination, and a mobile computing device, e.g., a tablet, for user interface and data processing.

Unfortunately, because the precision required of corneal topography devices for treating eye irregularities is greater than the precision required to treat DES, such devices tend to be more expensive than is necessary to provide reliable DES diagnosis and monitoring. In addition to being prohibitively costly, such DES treatment devices are typically non-portable, and only provided to medical professionals, meaning there is no way for patients to monitor DES at home.

Also known in the art are portable devices to be used with a smart phone for assessing and treating eye irregularities. As with other corneal topography devices, portable versions are prohibitively expensive, provide unnecessary capabilities, and are not optimized for DES diagnosis and treatment. For example, U.S. Pat. No. 9,839,352 discloses a corneal topography device that includes a Placido disc illumination system configured to be used with the camera of a mobile communication device.

Therefore, a clear need exists for an inexpensive and portable DES diagnosis and monitoring device that allows a DES patient to record and measure their dry eye condition themselves. Home DES monitoring allows a patient to monitor their condition day-to-day and compare their eye health under different treatments, behavioral changes, or exposure to different environments. For example, daily DES monitoring may allow a patient to assess the effectiveness of different eye drops, or determine the effect of a new brand of contacts.

These and other deficiencies of the prior art are addressed by one or more embodiments of the disclosed invention. Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out hereafter.

The features and advantages described in this disclosure and in the following detailed description are not all-inclusive. Many additional features and advantages will be apparent to one of ordinary skill in the relevant art in view of the drawings, specification, and claims hereof. Moreover, it should be noted that the language used in the specification has been principally selected for readability and instructional purposes and may not have been selected to delineate or circumscribe the inventive subject matter; reference to the claims is necessary to determine such inventive subject matter.

BRIEF DESCRIPTION OF THE DRAWINGS

Features and objects of the present invention and the manner of attaining them will become more apparent, and the invention itself will be best understood, by reference to the following description of one or more embodiments taken in conjunction with the accompanying drawings and figures imbedded in the text below and attached following this description.

Figure 1:
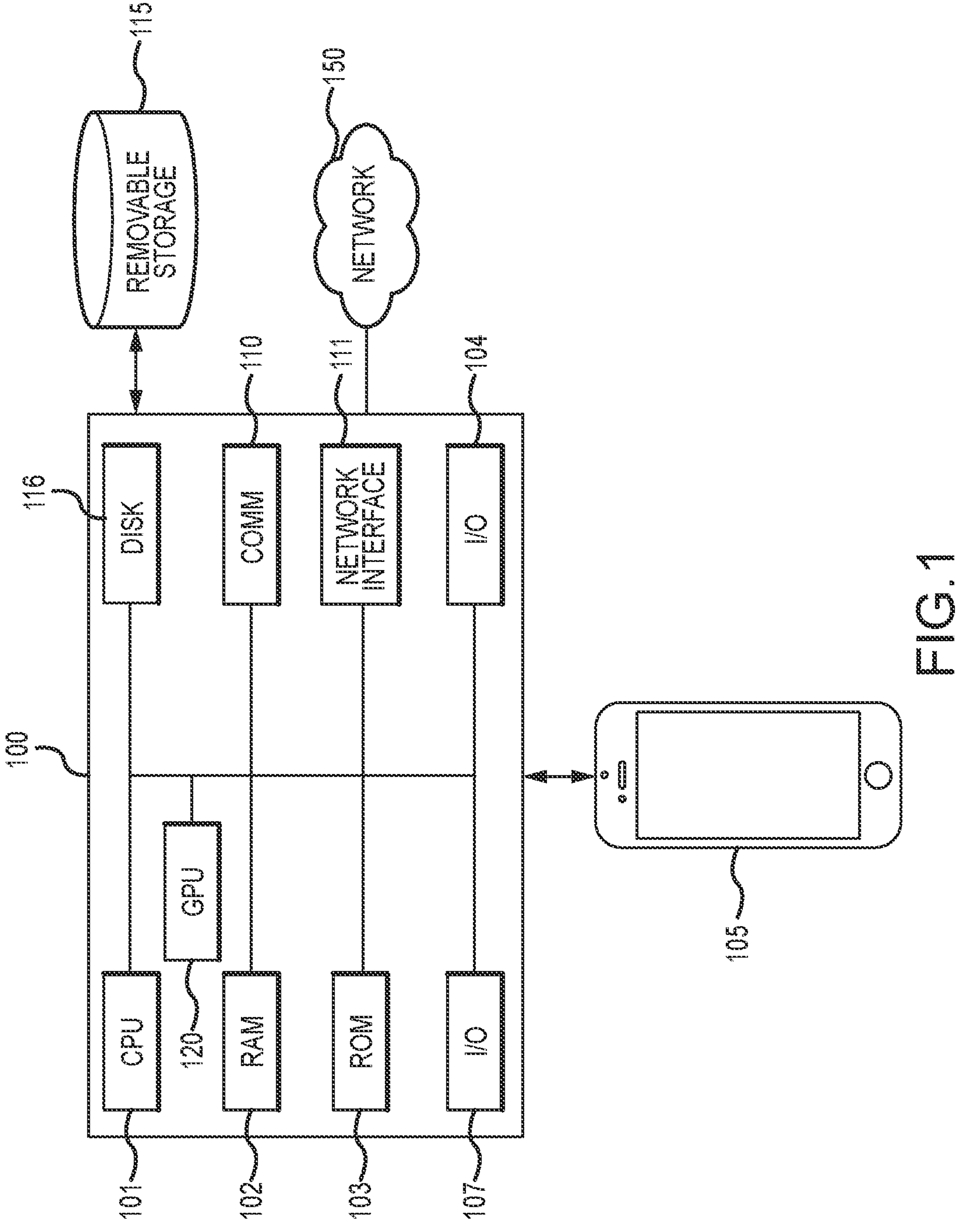
FIG. 1 depicts a high-level block diagram of a general-purpose mobile computer for executing elements of the disclosed invention.

The Figures depict embodiments of the present invention for purposes of illustration only. One skilled in the art will readily recognize from the following discussion that alternative embodiments of the structures and methods illustrated herein may be employed without departing from the principles of the invention described herein.

DEFINITIONS

Dry eye syndrome (DES) is a medical condition having various causes, and characterized by having dry eyes. DES is accompanied by related symptoms, such as eye irritation and redness, fluid discharge from the eyes, and eyes that tire easily. Symptoms may range from mild and occasional to severe and continuous. The condition is also known as keratoconjunctivitis sicca.

DESCRIPTION

The disclosed invention includes devices, systems, and methods for dry eye condition measurement and analysis that are intended for day-to-day use by laypeople. Disclosed are embodiments of an illuminator device, including a handheld version and a smartphone-mounted version. Also disclosed are embodiments of a mobile software application, and accompanying methods to perform dry eye syndrome diagnosis, assessment, and treatment. The illuminator devices are configured to perform anterior eye video recording, and can overlay such recordings with projected grid patterns. The app operates the illuminator, performs video analysis, computes dry eye-related parameters, summarizes the measured values, presents longitudinal data trends, and guides self-treatment. It also provides user administrative functions and facilitates data storage locally and on cloud servers.

The disclosed invention will now be described in detail with reference to several embodiments thereof as illustrated in the accompanying Figures. In the following description, specific details are set forth in order to provide a thorough understanding of embodiments of the disclosed invention. It will be apparent, however, to one skilled in the art that embodiments may be practiced without some or all of these specific details. In other instances, well known process steps and/or structures have not been described in detail in order to not unnecessarily obscure the invention. The features and advantages of embodiments may be better understood with reference to the drawings and discussions that follow.

It should be apparent to those skilled in the art that the described embodiments of the disclosed invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the disclosed invention as defined herein and equivalents thereto. Hence, use of absolute and/or sequential terms, such as, for example, "always," "will," "will not," "shall," "shall not," "must," "must not," "first," "initially," "next," "subsequently," "before," "after," "lastly," and "finally," are not meant to limit the scope of the disclosed invention as the embodiments disclosed herein are merely exemplary.

It will be also understood that when an element is referred to as being "on," "attached" to, "connected" to, "coupled" with, "contacting", "mounted" etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used to describe one element or feature's relationship to another element(s) or feature(s) as illustrated in the figures. Such spatially relative terms are intended to encompass different orientations of a device in use or operation in addition to the orientation depicted in the figures. For example, if a device in the figures is inverted, elements described as "under," or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

Included in the description are flowcharts depicting examples of the methodology which may be used in a travel system for individuals with cognitive disabilities. In the following description, it will be understood that each block of the flowchart illustrations, and combinations of blocks in the flowchart illustrations, can be implemented by computer program instructions. These computer program instructions may be loaded onto a computer or other programmable apparatus to produce a machine such that the instructions that execute on the computer or other programmable apparatus create means for implementing the functions specified in the flowchart block or blocks. These computer program instructions may also be stored in a computer-readable memory that can direct a computer or other programmable apparatus to function in a particular manner such that the instructions stored in the computer-readable memory produce an article of manufacture including instruction means that implement the function specified in the flowchart block or blocks. The computer program instructions may also be loaded onto a computer or other programmable apparatus to cause a series of operational steps to be performed in the computer or on the other programmable apparatus to produce a computer implemented process such that the instructions that execute on the computer or other programmable apparatus provide steps for implementing the functions specified in the flowchart block or blocks.

Accordingly, blocks of the flowchart illustrations support combinations of means for performing the specified functions and combinations of steps for performing the specified functions. It will also be understood that each block of the flowchart illustrations, and combinations of blocks in the flowchart illustrations, can be implemented by special purpose hardware-based computer systems that perform the specified functions or steps, or combinations of special purpose hardware and computer instructions.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Mobile Computer

One of reasonable skill will also recognize that portions of the present invention may be implemented on a general-purpose mobile computing system, such as a smartphone, a personal communication device, a mobile device, a notebook computer, a tablet, or the like. FIG. 1 is a generalized block diagram of a computer system in which software-implemented processes of the present invention may be embodied. As shown, system 100 comprises a central processing unit(s) (CPU) or processor(s) 101 coupled to a random-access memory (RAM) 102, a graphics processor unit(s) (GPU) 120, a read-only memory (ROM) 103, a touchscreen or user interface 106, a display or video adapter 104 connected to a display device 105, a mass storage device 115 (e.g., flash memory, disk, or the like), a fixed (mass) storage device 116 (e.g., flash memory, a hard disk), a communication (COMM) port(s) or interface(s) 110, and a network interface card (NIC) or controller 111 (e.g., cellular, Ethernet, WIFI). Although not shown separately, various antennae and a real time system clock is included with the system 100, in a conventional manner.

CPU 101 comprises a suitable processor for implementing the present invention. The CPU 101 communicates with other components of the system via a bi-directional system bus 120 (including any necessary input/output (I/O) controller 107 circuitry and other "glue" logic). The bus, which includes address lines for addressing system memory, provides data transfer between and among the various components. Random-access memory 102 serves as the working memory for the CPU 101. The read-only memory (ROM) 103 contains the basic input/output system code (BIOS), a set of low-level routines in the ROM that application programs and the operating systems can use to interact with the hardware, including reading characters from the touchscreen or keyboard, outputting characters to screens or printers, and so forth.

Mass storage devices 115, 116 provide persistent storage on fixed and removable media, such as magnetic, optical, or magnetic-optical storage systems, flash memory, or any other available mass storage technology. The mass storage may be shared on a network 150, or it may be a dedicated mass storage. As shown in FIG. 1, fixed storage 116 stores a body of program and data for directing operation of the computer system, including an operating system, user application programs, driver, and other support files, as well as other data files of all sorts. Typically, the fixed storage 116 serves as the main memory for the system.

In basic operation, program logic (including that which implements methodology of the present invention described below) is loaded from the removable storage 115 or fixed storage 116 into the main (RAM) memory 102, for execution by the CPU 101. During operation of the program logic, the system 100 accepts user input from a keyboard and pointing device, as well as speech-based input from a voice recognition system (not shown). The user interface permits selection of application programs, entry of keyboard-based input or data, and selection and manipulation of individual data objects displayed on the screen or display device 105. Likewise, the pointing device, such as a mouse, track ball, pen device, touch screen, or the like, permits selection and manipulation of objects on the display device. In this manner, these input devices support manual user input for any process running on the system.

The computer system 100 displays text and/or graphic images and other data on the display device 105. The video adapter 104, which is interposed between the display 105 and the system's bus, drives the display device 105. The video adapter 104, which includes video memory accessible to the CPU 101, provides circuitry that converts pixel data stored in the video memory to a raster signal suitable for use by a monitor or touchscreen. A hard copy of the displayed information, or other information within the system 100, may be obtained from a printer or other output device.

The system itself communicates with other devices (e.g., other computers) via the network interface card (NIC) 111 connected to a network (e.g., cellular network, Wi-Fi network, Bluetooth wireless network, or the like). The system 100 may also communicate with local occasionally connected devices (e.g., serial cable-linked devices) via the communication (COMM) interface 110, which may include a RS-232 serial port, a Universal Serial Bus (USB) interface, or the like. Devices that will be commonly connected locally to the interface 110 include laptop computers, handheld organizers, digital cameras, and the like.

The system itself communicates with other devices (e.g., other handheld devices or computers) via the NIC 111 connected to a network (e.g., cellular network, Wi-Fi network, Bluetooth wireless network, etc.). The system 100 may also communicate with local occasionally connected devices (e.g., serial cable-linked devices) via the COMM interface 110, which may include a RS-232 serial port, a Universal Serial Bus (USB) interface, or the like. Devices that will be commonly connected locally to the interface 110 include laptop computers, handheld computers, digital cameras, etc.

The system may be implemented through various wireless networks and their associated communication devices. Such networks may include modems, mainframe computers, or servers, such as a gateway computer or application server which may have access to a database. A gateway computer serves as a point of entry into each network and may be coupled to another network by means of a communications link. The gateway may also be directly or indirectly coupled to one or more devices using a communications link, or may be coupled to a storage device such as a data repository or database.

Portable DES Diagnosis and Monitoring Device

The disclosed invention includes devices, systems, and methods for the non-invasive diagnosis and treatment of DES in a portable format suitable for everyday use by patients. The invention includes a system comprising embodiments of an illuminator device for eye examination that is configured for use with a smartphone camera, and a software application (app) configured to run on a smartphone. Also included are methods for use of the system to perform DES diagnosis and treatment. Using the smartphone camera, the disclosed device records video imagery of a patient's eye. The accompanying app analyzes feature distortions on the ocular surface by performing feature extraction on the recorded video. Using such data, the app determines tear film break-up time and meniscus layer height, among other DES-relevant parameters. The app can compare these results to historical results gathered on a given individual, a baseline value for the individual, or a normalized baseline for healthy individuals to diagnose or measure the progression of DES.

Hand-Held Illuminator

Figure 2:
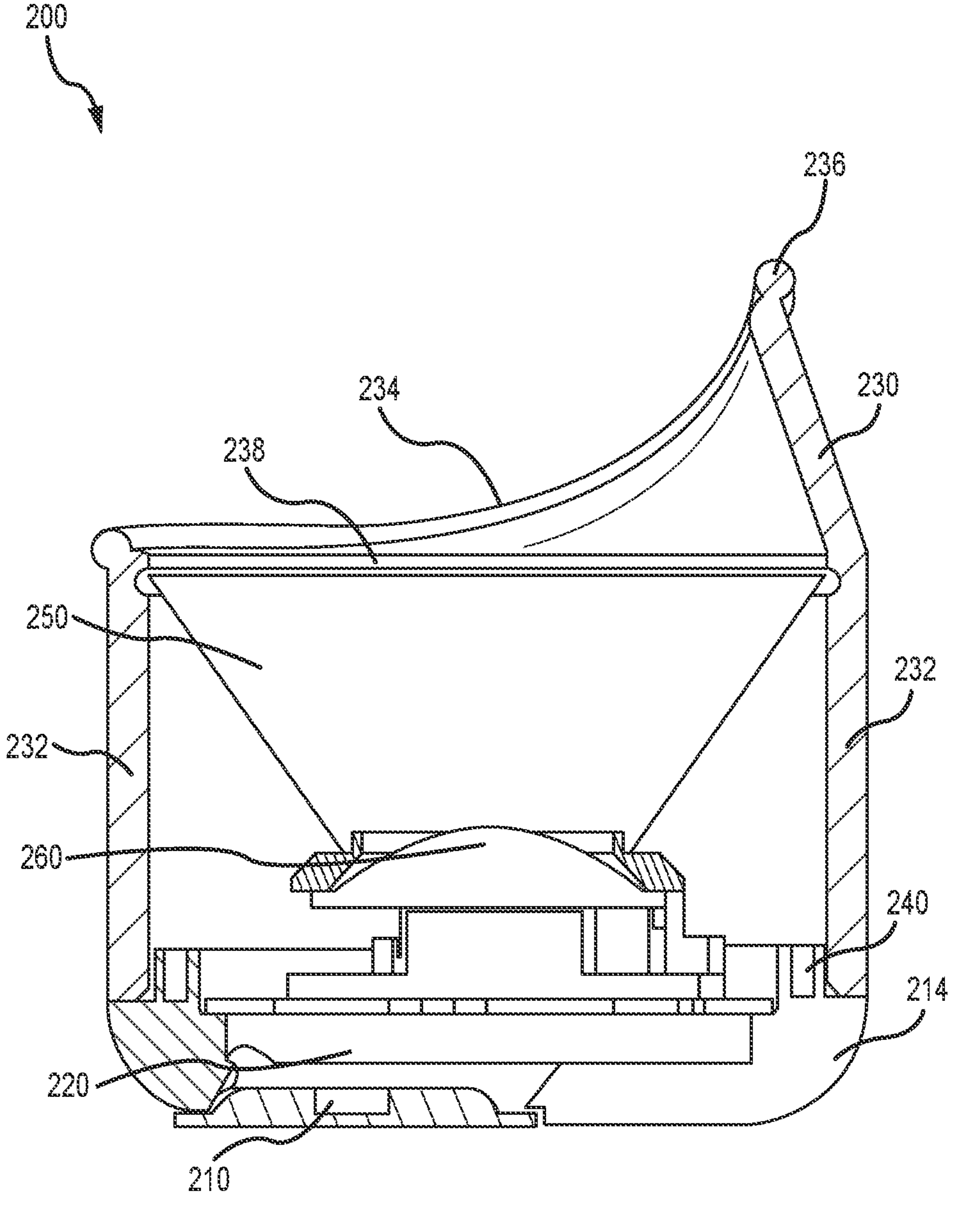
FIG. 2 depicts a top cross-sectional view of at least a portion of an embodiment of the disclosed invention.

With reference to FIG. 2, a top cross-sectional view of an illuminator device 200 of the disclosed invention is depicted. In some embodiments the illuminator 200 includes a camera 220 and is a self-contained hand-held device configured to connect to a smartphone via wired or wireless connection, such as a USB connection system, a near field communication system, a Bluetooth system, or other suitable connection. A power module 210 includes the camera 220, which is configured to capture videos of the cornea, and a power source such as a battery (not shown). In some embodiments, power is drawn from the mobile device through the USB connector. Because it has an onboard camera, and therefore does not need to physically mount on the mobile device to access the device's camera system, this embodiment is suitable for use with a wide variety of smartphones, tablets, or other mobile computers.

The camera 220 is housed in a first casing 214 that mechanically interacts with a second casing 230 to house the illuminator components. The second casing includes side walls 232 that attach to the first casing, and an eye cup 234 configured to ergonomically interact with an eye socket of a patient. The eye cup 234 may be shaped to conform to the patient's face to block out ambient light, and may include a rounded lip 236 to improve user comfort. The lip may be rubberized or covered with a flexible material such as foam rubber (not shown) to further improve comfort or to block out additional ambient light. Within the eye cup, the second casing includes an oculus 238 or opening that provides access to the patient's eye. The eye cup 234 is rotatably mounted so that it may be oriented to cover the right or left eye. As shown, the eye cup is oriented for placement over a patent's left eye. The eye cup would be rotated 180 degrees for placement over the patient's right eye. In the depicted embodiment, the second casing 230 rotates on the first casing 214 to allow the eye cup to rotate relative to the camera, but other arrangements are possible and contemplated.

Housed within the casings 214, 230, the illuminator includes a light ring 240 to provide illumination for device operation. The light ring includes a plurality of high intensity white lights arranged in a circular pattern around the camera, and may be, e.g., a plurality of white light emitting diodes (LED), or other suitable high intensity, low power light source. The light ring 240 receives power from the battery, and is configured to provide sufficient illumination for operation of a projector cone 250. Brightness of the light ring can be manually adjusted by use of a control knob (not shown), for example, to provide additional illumination of the cornea, or to reduce brightness for improved patient comfort.

The projector cone 250 comprises a transparent or translucent plastic film arranged in a truncated cone shape and is printed with a ring pattern. The cone has a narrow end that encircles the camera lens system 260, and a wide end that fits around the circumference of the oculus 238. The projector cone 250 is arranged so that light from the light ring 240 shines through the sides of the cone and projects the ring pattern onto the cornea. The projector cone 250 is removable and interchangeable with other projector cones that may be printed with different grid or ring patterns, each of which is suitable for a different application. The lens system 260 is situated between the camera 220 and the patient's eye, and focuses light entering the camera to provide suitably clear images of the patient's eye for DES diagnosis and treatment. Like the light ring, the lens system is powered by the battery.

Figure 3:
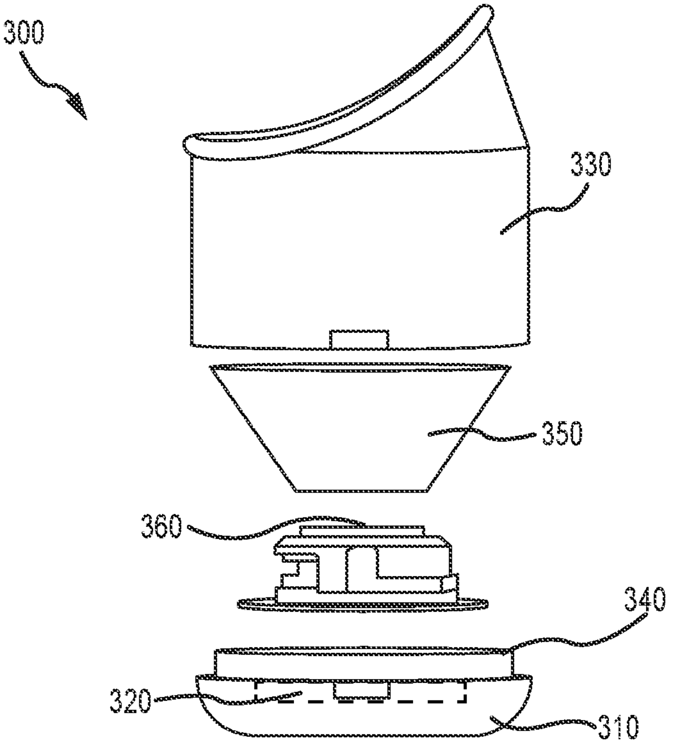
FIG. 3 depicts a top exploded view of at least a portion of an embodiment of the disclosed invention.

With reference to FIG. 3, an exploded view of the illuminator embodiment 300 of FIG. 2 is depicted, wherein like numbers refer to like components. Shown are the power module 310, the camera 320, the second casing 330, the light ring 340, the projector cone 350, and the lens system 360.

The illuminator 300 is configured for use with a software application hosted on a smartphone or other mobile device. The user (the user and patient may be the same individual) first connects the illuminator to the smartphone via, e.g., a USB connector or via Bluetooth, and controls and operates the illuminator through the app. From the app, the user activates the illuminator camera 320 to record video of a patient's eye. The user places the illuminator eye cup over the patient's eye socket, and the app accesses imagery from the camera. The app then uses a machine learning model to detect when the eye is in focus and correctly aligned within the projector cone 350 ring pattern. The app also uses video analytics to determine whether the left eye or the right eye is being imaged. Once focus and alignment conditions are met, the app automatically begins recording video and instructs the patient to perform a series of blinks. The app then evaluates whether a video of the eye of acceptable quality has been captured, including checking the blink sequence, the length of video, the eye alignment, and focus. When a suitable video is recorded, the app informs the user, and performs analysis on the recorded video. Then the app reports the results to the user.

Mounted Illuminator

Figure 4:
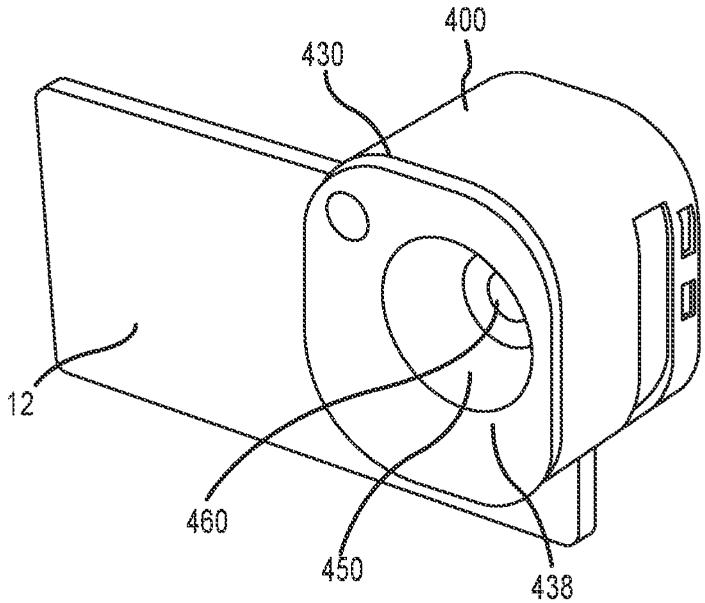
FIG. 4 depicts a perspective view at least a portion of an embodiment of the disclosed invention shown mounted on a mobile computer.

With reference to FIG. 4, an embodiment of the illuminator configured to be mounted on a smartphone and to use the smartphone's internal camera is depicted. The illuminator 400 is shown mounted on a smartphone 12 with the lens system 460 and projector cone 450 aligned over the smartphone camera (not shown). The second casing 430 includes an oculus 438, through which (in this diagram) can be seen the projector cone 450 and the lens system 460.

Figure 5:
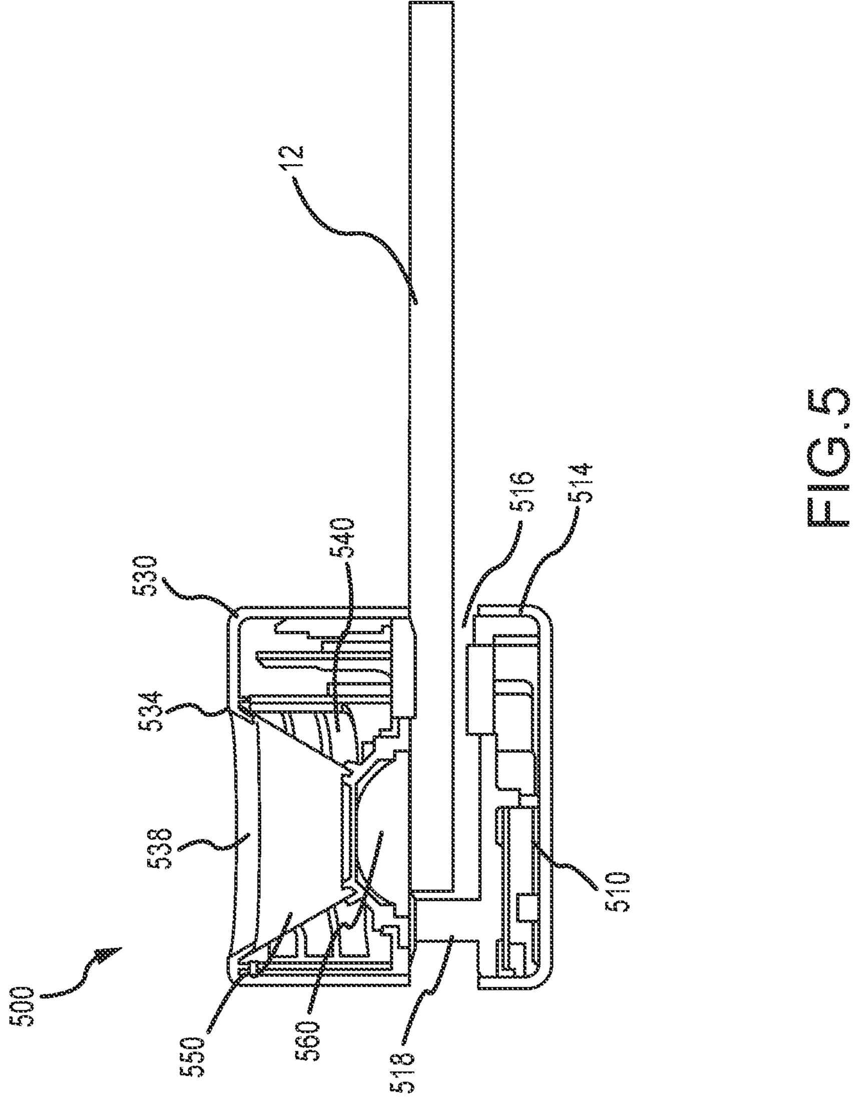
FIG. 5 depicts a top cross-sectional view of at least a portion of an embodiment of the disclosed invention, shown mounted on a mobile computer.

With reference to FIG. 5, a cross-sectional view of the mounted illuminator 500 is depicted. In this embodiment a docking slot 516 is located between the first casing 514 and the second casing 530, and is configured to accommodate a smartphone 12 and removably secure it in place. A bridge 518 connects the first casing to the second casing, and provides electrical connection between the battery located in the power module 510 and the components in the second casing. The bridge also serves to position the smartphone so that the smartphone camera is properly aligned with the lens system when the phone is fully seated within the slot 516. As with the previous embodiment, the mounted illuminator also includes a light ring 540, an interchangeable projector cone 550, an oculus 538, and a rotatable eye cup 534. Similarly, the mounted illuminator may be powered through the smartphone's USB port, rather than from an onboard power source.

Also like the previous embodiment, the mounted embodiment is operated through the software application run on the smartphone. The user/patient first mounts the illuminator onto the smartphone by sliding the smartphone into the mounting slot until the phone is seated in place. The illuminator is then connected to the smartphone via USB connector or other suitable means, e.g., near field communication system, Bluetooth, etc., and the user controls and operates the illuminator through the app. The user places the illuminator eye cup over the patient's eye socket, and the app accesses imagery from the smartphone camera. From the app, the user activates the smartphone camera to record video of a patient's eye. The remainder of the app functionality is similar to the previous embodiment.

Some embodiments of the mounted illuminator are configured with an alternate system for activating the smartphone camera. In such embodiments, illuminator is further equipped with an electromagnet (not shown) powered by the power source and electronically connected to the light ring. The app is further configured to monitor the smartphone compass for variations. When the app is used to turn on the light ring, the electromagnet is also turned on, creating a small change in the magnetic flux captured by the compass. The app detects the change detected by the compass and activates the camera to record video of the cornea. The electromagnet system adds a backup actuation means to ensure the smartphone camera activates on time in the event the app's camera focus and alignment determinations do not consistently initiate video recording.

The illuminator embodiments described herein improve on existing DES systems in several ways, three of which are identified here. The first improvement is reduced ring pattern complexity. Placido rings or keratoscopes used to identify eye irregularities project a detailed, fine ring pattern onto the eye to determine the curvature of the cornea, which has much higher precision requirements than DES treatment. As disclosed, the illuminator uses a much-simplified projected Placido ring pattern designed for use with the discrete light sources of the light ring. The light sources are arranged along the ring so that when they shine through the projector cone and reflect of the cornea, they provide the necessary illumination and reference points for the app to determine various metrics relevant to DES. The simplified ring pattern need only provide consistent features with which to compare the distortion of light as it reflects off the fluid coating the eye.

Another advantage of the disclosed DES treatment system is the shape of the eye cup, which automatically aligns the camera with the patient's cornea and simplifies camera focusing. When the user/patient fits the eye cup over the eye, the camera self-aligns with, and is located a fixed distance from, the cornea. The eye cup thus allows self-testing by eliminating the need for a trained user, or reliance on camera autofocus. The eye cup design also improves the quality of images and thus improves result consistency by limiting interference from ambient light.

Finally, embodiments of the disclosed DES device perform automatic eye placement recognition. The rotatable eye cup allows use of the illuminator on either the left or the right eye without changing illuminator orientation, and application software uses video analytics to recognize which eye is it facing. The illuminator system can therefore calibrate its analysis for the appropriate eye without reliance on gyroscope information.

Software Application

The mobile software application is the primary system for providing operational, analytic, and general functionalities for DES diagnosis and treatment through use of the illuminator device. As described above, the app controls illuminator operational functions, including left or right eye detection, camera focus and alignment, light ring activation, and anterior eye video recording. Certain of these functions, including left or right eye detection and camera focus and alignment are performed using machine learning models. Video recording also includes issuing instructions to the patient for when to blink, as well as performing an initial video quality assessment.

The app also performs digital image processing on the recorded video to allow DES analysis and parameter measurement. The app uses image processing techniques in conjunction with deep learning algorithms to perform object detection and segmentation of the anterior eye images. Using such techniques, the app can recognize the locations of the iris and lower tear meniscus, and recognize when an eyelid is closed or open during a blink. Once features are identified, the app performs segmentation of relevant features, e.g., the lower tear meniscus. The app also uses the ring pattern from the projector cone to divide the eye into separate regions, and performs image segmentation on each region. Image processing is sophisticated enough to ignore certain image artifacts, such as eyelash shadows or other image imperfections.

Once it completes object detection and image segmentation on the recorded video, the app can analyze the processed images to characterize parameters relevant to DES. For example, the app uses the ring pattern segmentation to perform a grid projection deformation analysis. The deformation analysis allows the app to measure the tear film breakup time, as well as the tear meniscus height. Recognition of blink events and timing their frequency allows the app to characterize a blink rate. Analysis results can be refined or corrected based on user observations or user review of intermediate data. The app may also compare corneal lip imagery with example interferometric patterns to perform corneal lip layer interferometric pattern recognition. Corneal lip layer analysis may also be accomplished manually if insufficient data is collected, requiring the user to manually compare the corneal lip images to known interferometric patterns.

Besides the operational, image processing and analysis functions, the app also provides some general functionalities. These include administrative functions, such as user registration and login, as well as results reporting and summarization. A user/patient can access a report on the current eye scan results, or generate a historical trend report over a selected period. The app can also provide dry eye self-treatment instructions and suggestions based on a patient's current or historical results. The app can also send smartphone notifications to the patient, such as a prompting a regular eye scan, or prompting eye drop administration or other self-treatments. Finally, the app has connectivity functionalities to provide a patent's eye scan data to a cloud server for storage, intermediate processing or analysis, or advanced data processing or analysis.

Figure 6:
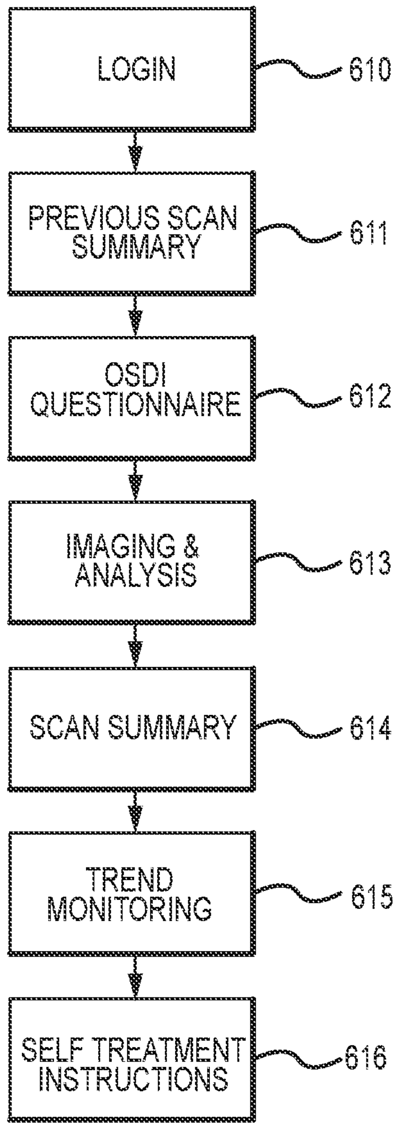
FIG. 6 depicts a flow chart showing an example user-performed sequence according to an embodiment of the disclosed invention.

With reference to FIG. 6, a flow chart is depicted summarizing an example process for an existing user to use the application and illuminator to perform DES treatment. A user and/or patient accesses the software application on a smartphone and is presented a login prompt, where the user can log in 610. Once logged in, an existing user is automatically presented a summary of their last eye scan results 611. When the user has completed their review of their previous scan, they can navigate to the Ocular Surface Disease Index (OSDI) questionnaire 612 where they must respond to the questionnaire prompts. Once the questionnaire is complete, the app guides the user to perform anterior eye imaging and analysis 613, which step includes several sub-steps. First the app guides the user to complete video recordings of each eye, once with the projected Placido ring pattern and once without the ring pattern. Then the app guides the user to check the video quality. If the quality of a video is inadequate, the user will be guided through re-taking the deficient video(s).

Once videos of sufficient quality are acquired, the app performs digital image processing, and performs analysis on the videos. The app will then instruct the user to perform manual adjustments to intermediate or final results if such adjustments are required by change criteria. Once the analysis is complete, the app provides the user a summary page displaying the current eye scan results 614. If longitudinal data is available, i.e., the user has performed multiple eye scans over a period of time, the app will prompt the user to select a time period for the display of trend data, and the app will produce a trend report 615 for the user to compare eye health over the course of the reported period. Finally, the app will provide the user with tailored self-treatment suggestions, eye care tips, and useful external links related to DES based on the user's reported current and historical results 616.

Figure 7:
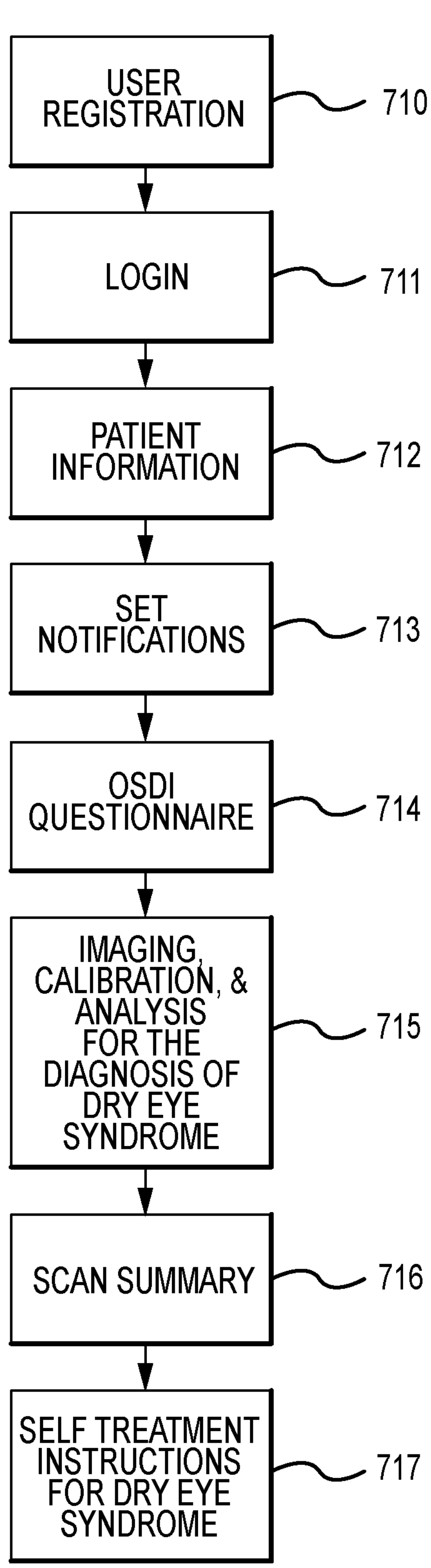
FIG. 7 depicts a flow chart showing an example user-performed sequence according to an embodiment of the disclosed invention.

With reference to FIG. 7, a flow chart is depicted summarizing an example process for a new user to sign up, login, and use the application and illuminator to perform DES treatment for the first time. First a user and/or patient accesses the software application on a smartphone and is presented a login prompt, where the user can sign up for an account 710 and login 711. Once logged in, the app directs the new user to an information page 712 where the user is prompted to provide details about their eye condition, history of treatment, the medications they are taking, physician contact information, etc. Next, the app directs the new user to a notifications settings page 713, where the user is prompted to provide notifications preferences, such as when the app should send eye drop use reminders, when and how frequently the user would like the app to remind them to perform an eye scan, e.g., daily, every two days, once a week, etc., and when and how the app should notify them to perform self-treatment. The app then directs the new user to the OSDI questionnaire 714 where they must respond to the questionnaire prompts. Once the questionnaire is complete, the app guides the user to perform anterior eye imaging and analysis 715, which step includes several sub-steps, for the diagnosis of dry eye syndrome. First the app guides the user to anterior eye imaging complete video recordings of each eye, once with the projected Placido ring pattern and once without the ring pattern. Then the app guides the user to check the video quality. If the quality of a video is inadequate, the user will be guided through re-taking the deficient video(s). The app then performs image calibration on the new user's video recordings. Once the app has calibrated to the new user, the remaining step in the process, including digital image processing, analysis, presenting the scan summary 716 and providing self-treatment recommendations 717 for dry eye syndrome similar to that for an existing user.

Figure 8:
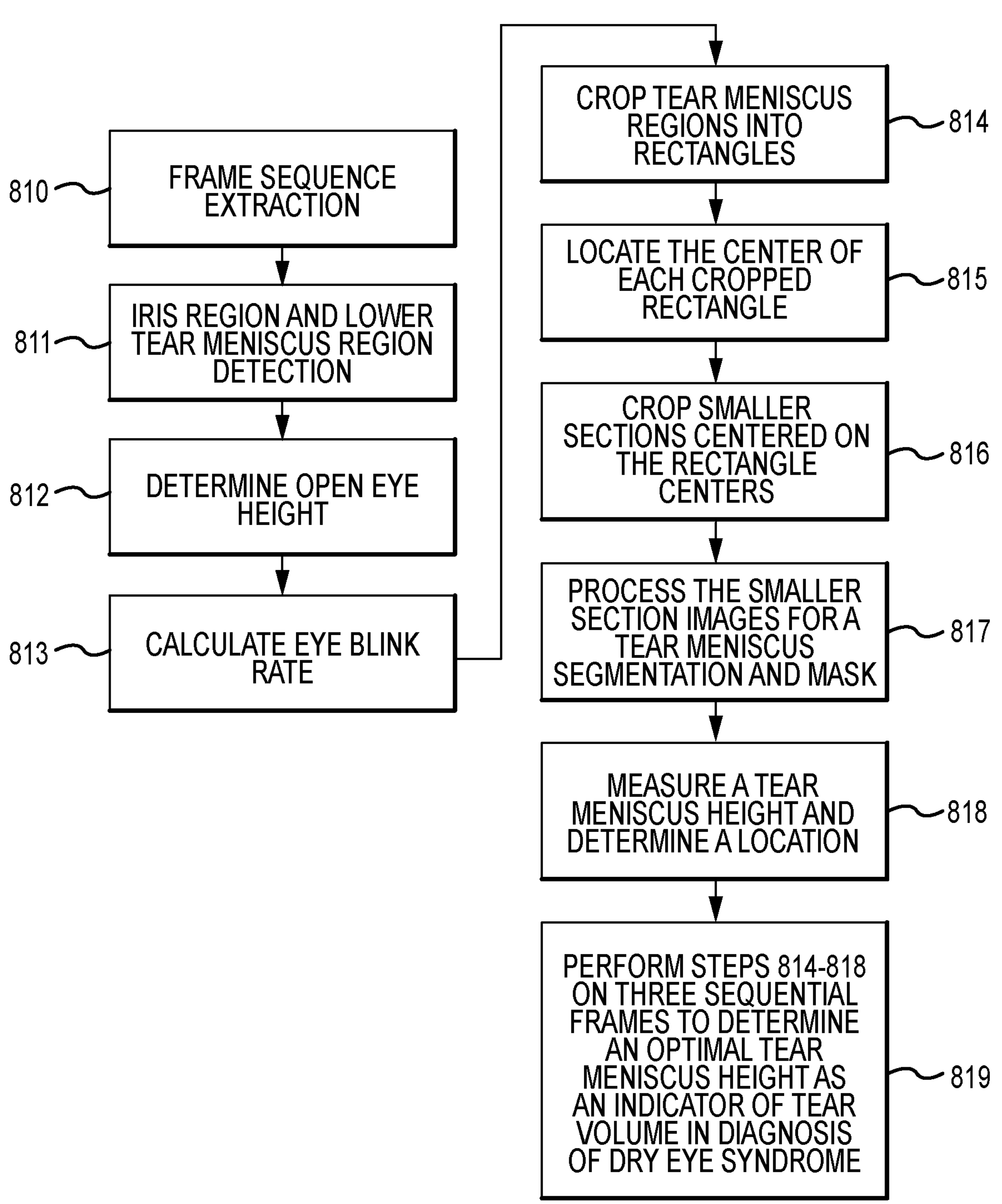
FIG. 8 depicts a flow chart showing a method of dry eye syndrome diagnosis or treatment according to an embodiment of the disclosed invention.

With reference to FIG. 8 a flow chart is depicted showing an example method for performing object identification, digital image processing, and parameter measurement on extracted frames from a video of the anterior eye as recorded by an illuminator device. The method includes frame sequence extraction, i.e., extracting individual frames in sequence at a defined interval over a defined period, e.g., a frame is extracted every 100 or 200 milliseconds over a period of 10 seconds, from a video recording of the anterior eye 810. Next, the method uses a trained deep learning model to process each frame and detects an iris region and a lower tear meniscus region in each frame 811. The method measures a height dimension of the detected iris regions to determine the height dimension of an open eye 812, which will be the maximum height of all detected iris regions. From the open eye height, the method compares iris region height across sequential frames to calculate an eye blink rate 813.

The method then uses the detected lower tear meniscus regions to perform analysis. First the method isolates the detected tear meniscus regions from each frame by cropping out a rectangular image of the tear meniscus region 814. Then the method locates the center of each cropped rectangle 815, and crops out a smaller section, e.g., 200×100 pixels centered on the rectangle center 816. The method then uses another trained learning model to perform digital image processing on the smaller sections, which yields a segmentation and mask of the tear meniscus 817. The method next uses the tear meniscus mask to measure a tear meniscus height and determine a tear meniscus location 818. The method performs steps 814 through 818 on three consecutive frames, and uses the results to determine an optimal tear meniscus height 819 as an indicator of tear volume in the diagnosis of dry eye syndrome.

Figure 9:
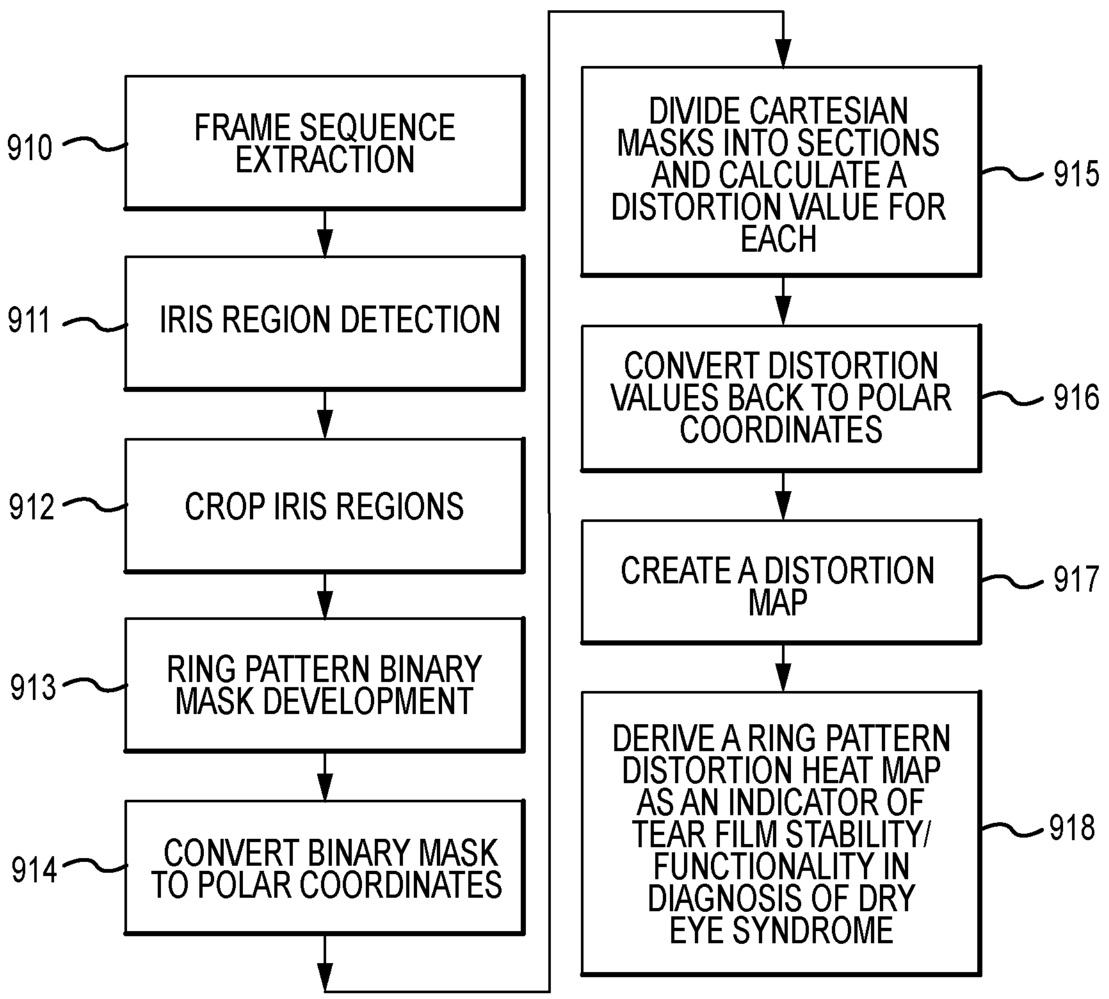
FIG. 9 depicts a flow chart showing a method of dry eye syndrome diagnosis or treatment according to an embodiment of the disclosed invention.

With reference to FIG. 9 a flow chart is depicted showing an example method for performing ring pattern distortion analysis. The method includes recording anterior eye video with a projected Placido ring pattern and performing frame sequence extraction 910. Then, iris region detection is performed on each frame, and iris region masks are created 911. The iris region marks are then cropped and extracted from the frames 912. The cropped iris regions are processed using a threshold method to develop a ring pattern binary mask for the iris region 913. Then the center of the Placido ring pattern is detected and used as the origin of a set of polar coordinates. The binary masks are then converted to cartesian coordinates 914, and the cartesian binary ring pattern masks are divided into smaller sections. An object edge slope accumulation method is applied to the smaller sections and a ring pattern distortion value is calculated for each section 915. The distortion values are arranged in a matrix and converted back to polar coordinates 916. The polar distortion values are then used to create a ring pattern distortion map 917. Finally, the distortion map is interpreted and a distortion heat map is derived 918 as an indicator of tear film stability/functionality in diagnosis of dry eye syndrome. The distortion heat map displays distortion values in terms of colors, numbers, or other suitable index, e.g., high distortion levels are characterized as red or 5, low distortion level are green or 1, etc.

Figure 10:
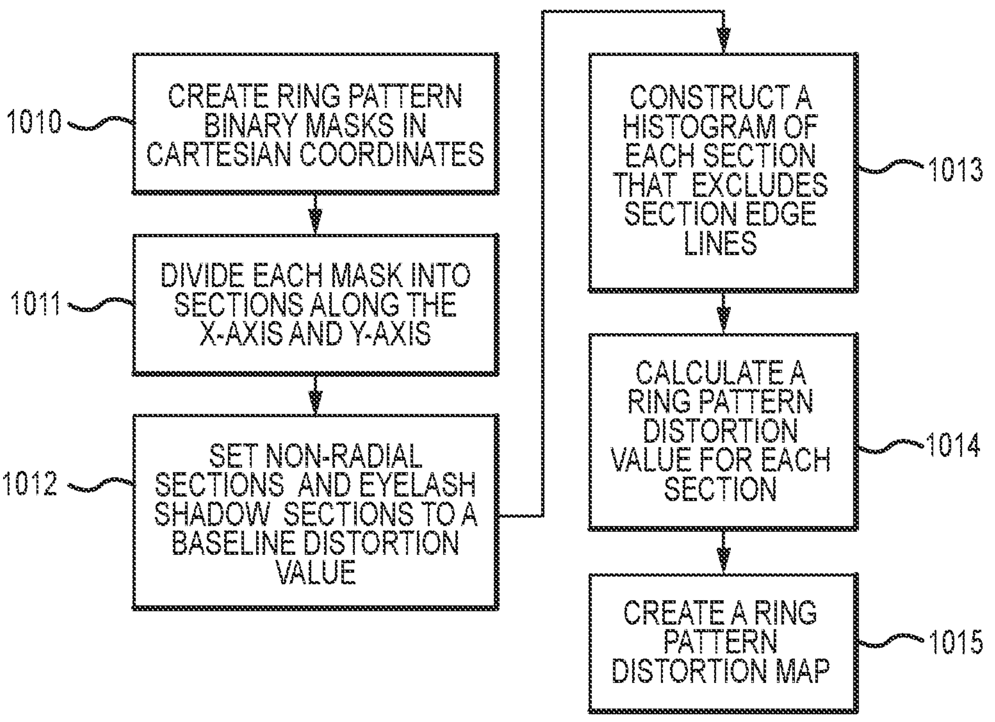
FIG. 10 depicts a flow chart showing a method for dry eye syndrome diagnosis or treatment according to an embodiment of the disclosed invention.

With reference to FIG. 10, a flow chart is depicted showing an example method for creating a ring pattern distortion map. The method includes recording anterior eye video with a projected Placido ring pattern and performing frame sequence extraction. Then, iris region detection is performed on each frame, and iris region masks are created. The iris region marks are then cropped and extracted from the frames. The cropped iris regions are processed using a threshold method to develop a ring pattern binary mask for the iris region. Then the center of the Placido ring pattern is detected and used as the origin of a set of polar coordinates. The binary masks are then converted to cartesian coordinates 1010, and the cartesian binary ring pattern masks are divided into segments of 50×50 pixels along the x-axis and y-axis in the cartesian coordinate system 1011. Then the method excludes sections not found within the radians of the ring pattern, as well as those sections containing eyelash shadows and sets their distortion values to a predefined base value 1012. Next the method constructs a histogram for each section 1013. Histogram construction includes identifying all the objects in the section, identifying points along the boundaries of each object, and finding the contour slopes of each of the boundary points. Slope values of the four section edges are excluded from the histogram. Then the method calculates a ring pattern distortion value for each section using the section's histogram 1014. The section histogram values are weighted according to weighting parameters multiplied by the histogram values of the adjacent sections. Finally, a ring pattern distortion map of the eye is created by assembling the distortion values for each section 1015.

Graphical User Interface

Figure 11:
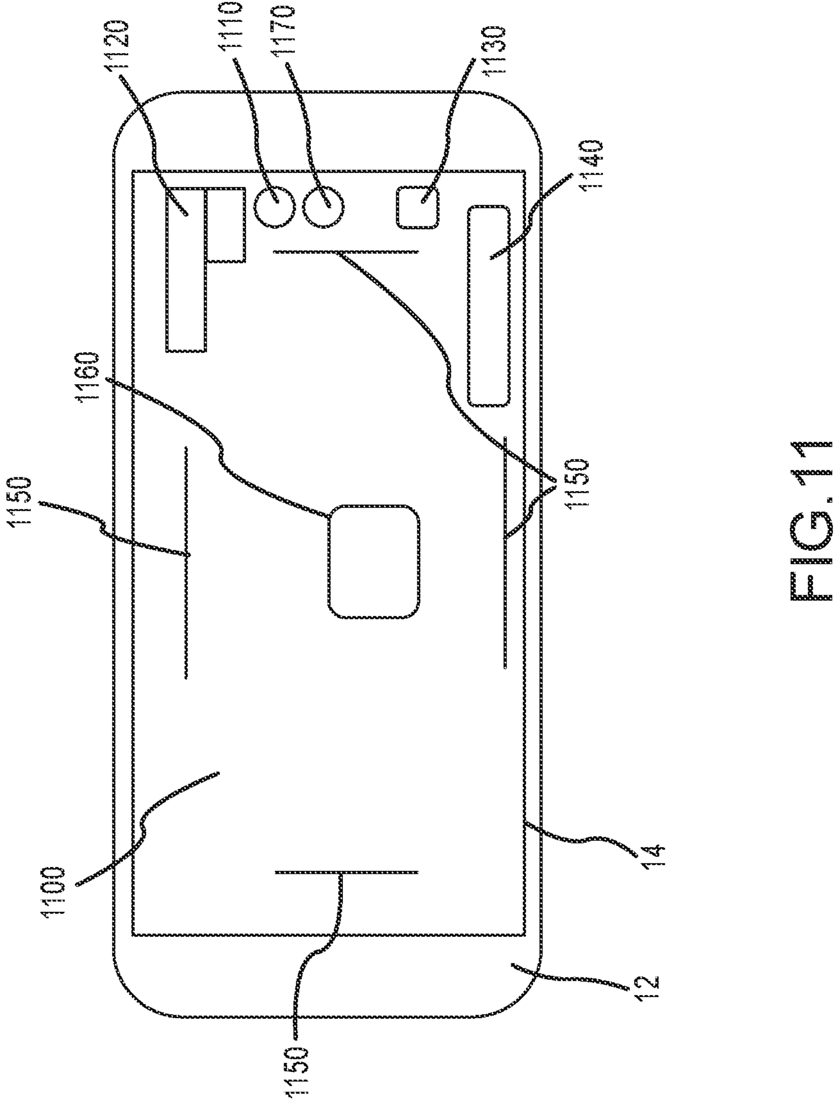
FIG. 11 depicts an example graphical user interface (GUI) according to an embodiment of the disclosed invention, as displayed on a mobile computer.

With reference to FIG. 11, an example Graphical User Interface (GUI) layout for video recording 1100 is depicted. The GUI is generated by the software application for use with the disclosed illuminator and displayed on the touchscreen area 14 of a mobile device 12 such as a smartphone. A record button 1110 when activated alternately starts and stops a video recording process. A text field 1120 displays recording information, such as video recording duration, identifies the eye being recorded, indicates whether the ring pattern is illuminated, and/or other pertinent information. A help button 1130 when activated alternately displays or hides a pop-up window that contains help information, and may include a help topic search function, or a list of help topics, etc. A slider 1140 controls the zoom function of the camera, and operates, for example, so that the camera is fully zoomed out when the slider is positioned to the left of the field, and fully zoomed in when the slider is at the right of the field. Four boundary guides 1150 indicate the area within which the eye should be contained for a quality video recording of the anterior eye. A pupil locator 1160 should be centered on the pupil for proper camera alignment with the eye. An accept button 1170, when activated, allows the user to accept the recorded video and return to the original view of the recording screen 1100 so that additional video may be recorded.

Figure 12:
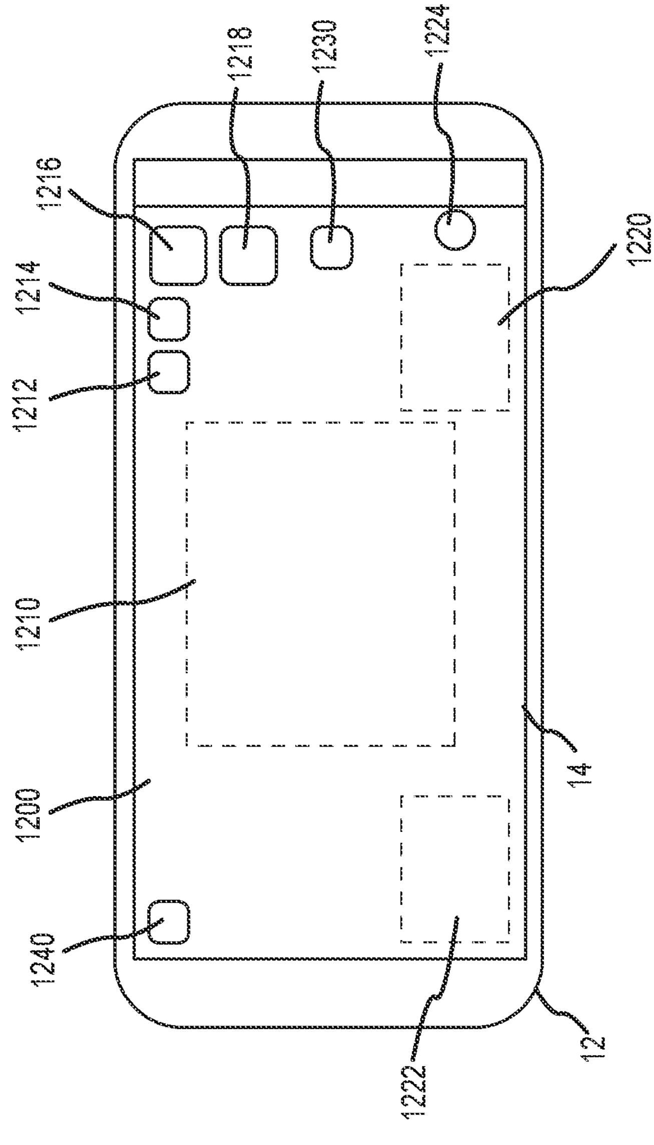
FIG. 12 depicts an example GUI according to an embodiment of the disclosed invention, as displayed on a mobile computer.

With reference to FIG. 12, an example GUI layout for tear meniscus height and iris interferometric pattern analysis 1200 is depicted. The GUI is generated by the app and displayed on the touchscreen area 14 of a mobile device 12. A primary display window 1210 is used to display either a segmented tear meniscus region image or a segmented iris region image depending on activation of a meniscus selector button 1212 or an iris selector button 1214. A left eye selector button 1216 when activated causes images from the left eye to be displayed in the display window 1210, and similarly a right eye selector button 1218 causes images from the right eye to be displayed. A manual adjustment controller 1220 contains three sliding bar controllers (not shown), and is used to adjust a detected rectangular region overlaying the image displayed in the display window 1210. One bar controller adjusts the height of the rectangular region, a second bar controller adjusts the x-axis, and a third bar controller adjusts the y-axis. Another button 1222 does something. A reset button 1224 returns the rectangular region to the original detected condition if manual adjustment is unsatisfactory. A text field displays blink rates, tear meniscus heights, tear film interferometric patterns, left or right eye selection, or other suitable messaging. A help button 1230 when activated displays help information as previously described, and a back button 1240 when activated returns the user to the previous step.

Figure 13:
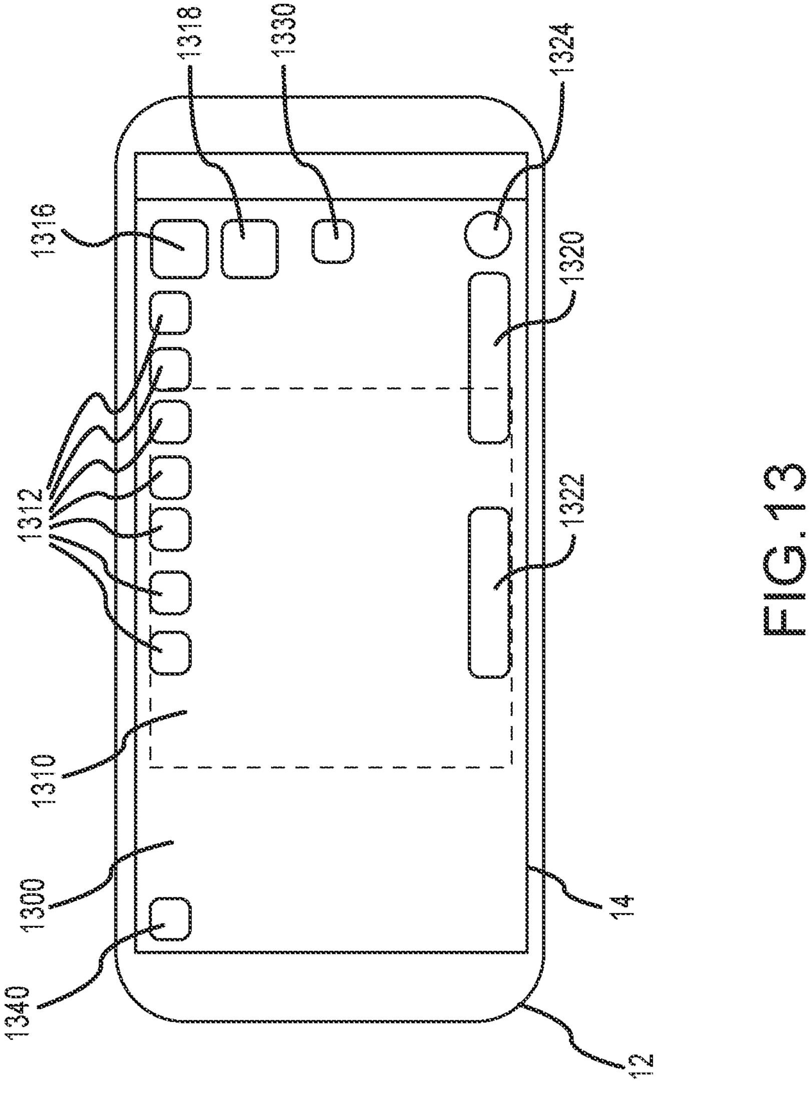
FIG. 13 depicts an example GUI according to an embodiment of the disclosed invention, as displayed on a mobile computer.

With reference to FIG. 13, an example GUI layout for a Placido ring pattern projection image with an overlaid Placido ring distortion heatmap 1300 is depicted. The GUI is generated by the app and displayed on the touchscreen area 14 of a mobile device 12. The GUI has a primary display window 1310 for displaying the Placido ring pattern projection with overlaid Placido ring distortion heatmap, as selected. A group of seven image selector buttons 1312 when activated allow the user to select a specific frame image from a video to be displayed in the display window 1310. A left eye selector button 1316 when activated causes images from the left eye to be displayed in the display window 1310, and similarly a right eye selector button 1318 causes images from the right eye to be displayed. A text field 1320 displays the detected non-invasive tear film breakup time (NiBUT) as generated by the app, and also functions as a text editor field, allowing the user to manually input a NiBUT value if desired. A sliding bar controller 1322 allows the user to change the opacity of the overlaid heatmap image displayed in the display window 1310, e.g., if the bar is positioned to the left, the heatmap image is fully opaque, and if the bar is positioned on the right, the heatmap image is fully transparent. A reset button 1324 returns the NiBUT value to the value generated by the app if the user decides a manual change is unsatisfactory. A help button 1330 when activated displays help information as previously described, and a back button 1340 when activated returns the user to the previous step.

Figure 14:
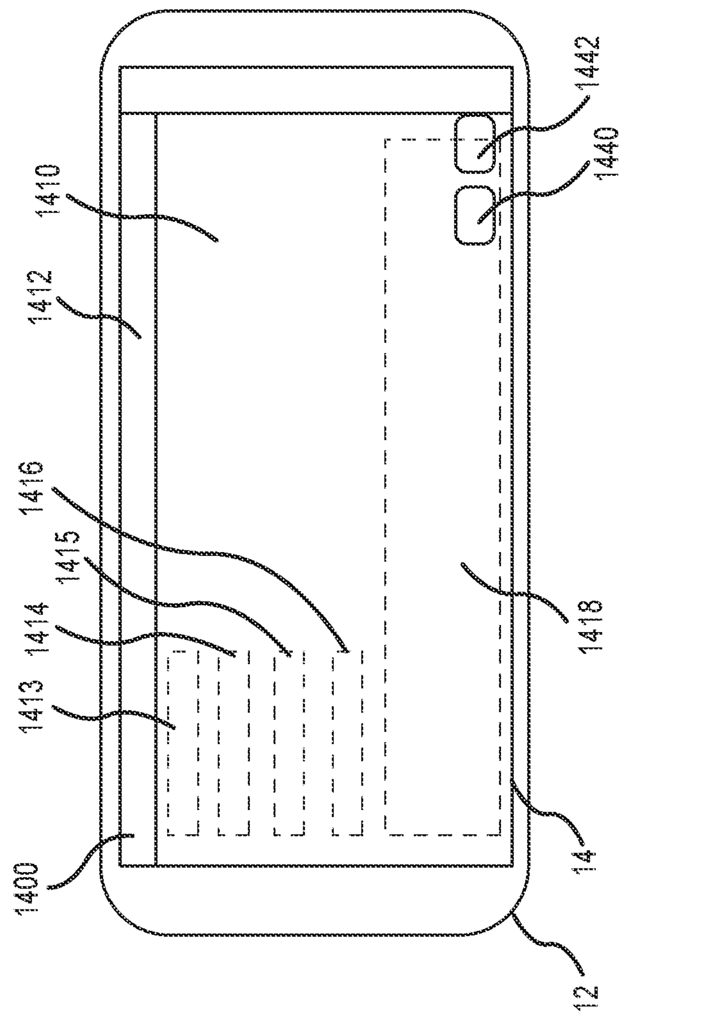
FIG. 14 depicts an example GUI according to an embodiment of the disclosed invention, as displayed on a mobile computer.

With reference to FIG. 14, an example GUI layout for a scrolling summary display of current measures and analysis 1400 is depicted. The GUI is generated by the app and displayed on the touchscreen area 14 of a mobile device 12. The scrolling summary page 1410 shows all measured data and analysis results derived from the left eye and right eye videos in a sequential manner, wherein the user can use a pair of buttons, a back button 1440, and a next button 1442 to navigate through the data set. The scrolling display includes a fixed title window 1412, which identifies the portion of information being displayed on the scrolling page 1410. A series of text fields 1413, 1414, 1415, 1416, identifies or labels the type of information being displayed and includes the numerical value of the information. For example, the text fields may show a blink rate, an iris interferometric pattern, a tear meniscus height, a distortion heat map, or other result as follows: "Blink Rate: 20/min"; "Tear Meniscus Height: 0.15 mm," etc. A visual display window 1418 shows results requiring a visual representation, such as a distortion heatmap, a frame of recorded video, cropped iris section, etc.

Figure 15:
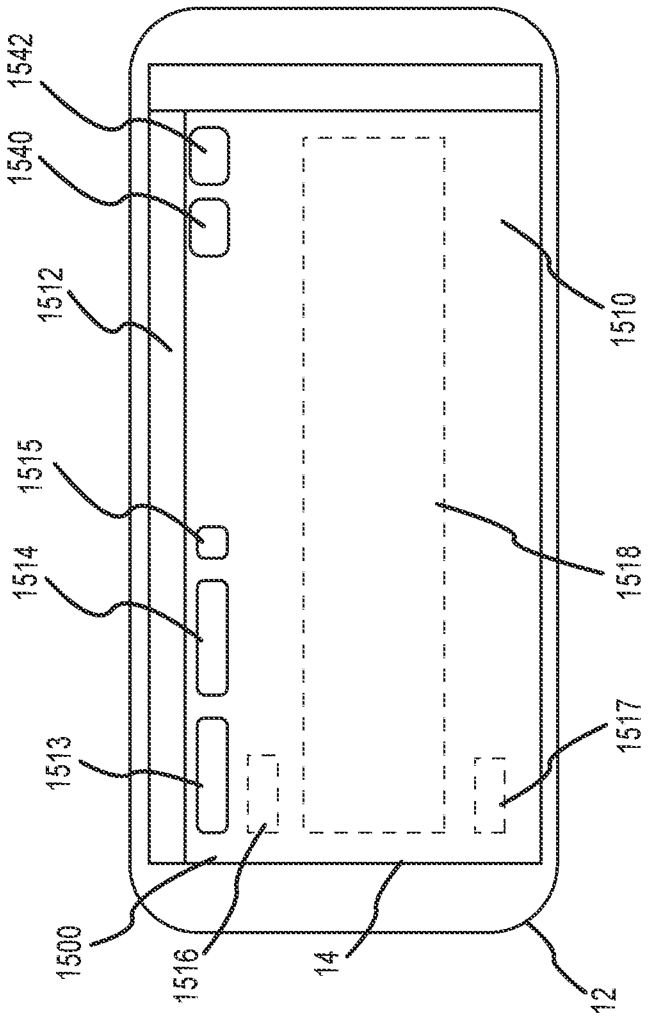
FIG. 15 depicts an example GUI according to an embodiment of the disclosed invention, as displayed on a mobile computer.

With reference to FIG. 15, an example GUI layout for a scrolling trend data display 1500 is depicted. The GUI is generated by the app and displayed on the touchscreen area 14 of a mobile device 12. The scrolling summary page 1510 shows a period of trend data that can be navigated in a sequential manner, wherein the user can use a pair of buttons, a back button 1540, and a next button 1542, to navigate through the data set. The scrolling display includes a fixed title window 1512, which identifies the time period of trend information being displayed on the scrolling page 1510. A starting date field 1513 is for inputting and displaying a start date for the trend data, and an end date field 1514 is for inputting and displaying an end date for the trend data. A data retrieval button 1515, when activated, refreshes the displayed information to match the start and end dates entered in their respective fields 1513, 1514. An OSDI field 1516 is for displaying the OSDI Score during the selected time period. A visual display window 1518 displays diagrams relevant to the selected time period arranged by alphabetical order according to the diagram title. A summary button 1517, when activated, displays summary content.

Figure 16:
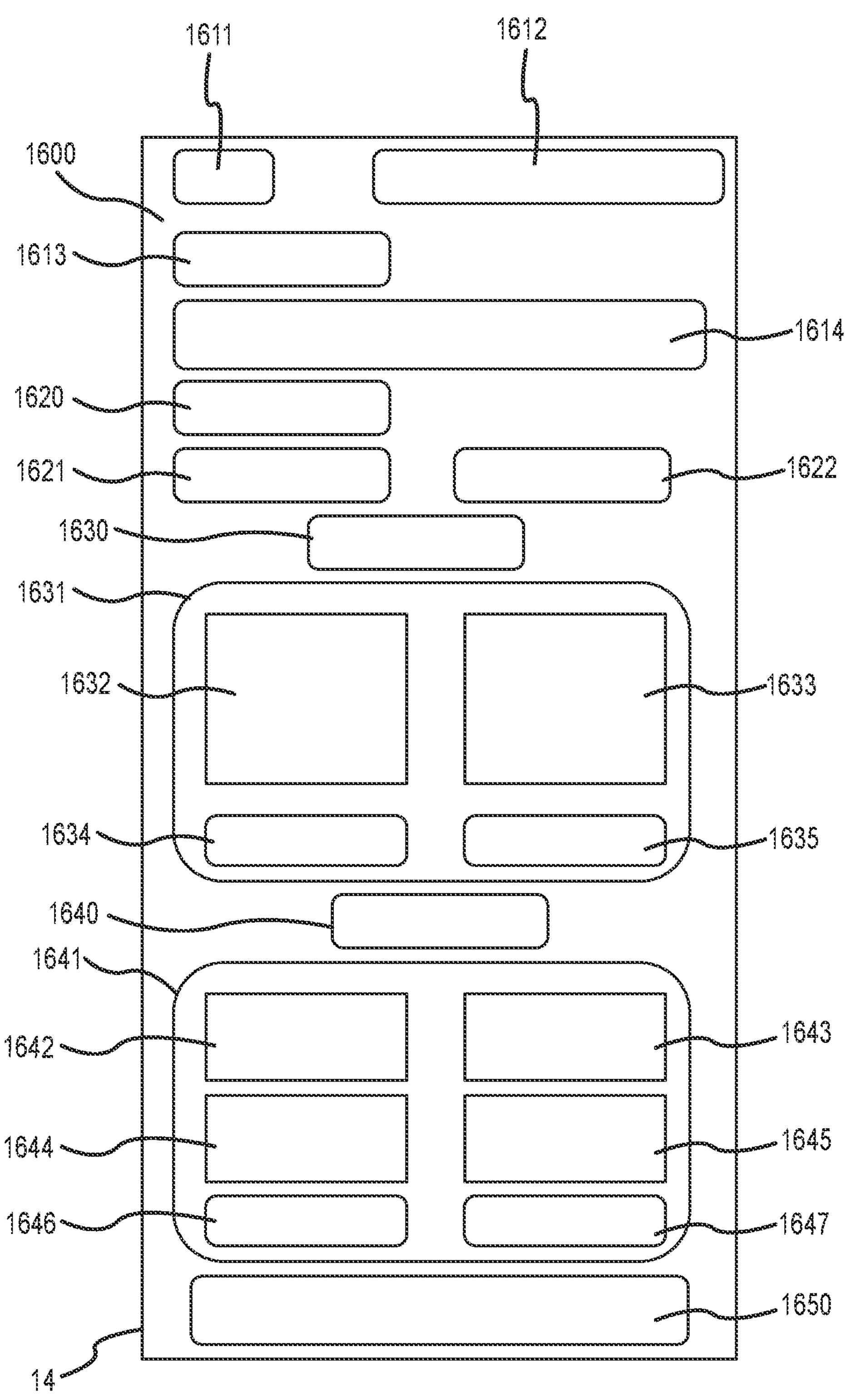
FIG. 16 depicts an example GUI report layout according to an embodiment of the disclosed invention, as displayed on a mobile computer.

With reference to FIG. 16, an example GUI layout for an eye scan report 1600 is depicted. The GUI is generated by the app and displayed on the touchscreen area 14 of a mobile device (not shown). A logo window 1611 displays a company logo, and a title window 1612 lists the title of the displayed report. A date window 1613 displays the date the eye scan was performed, and the name of the service provider, if applicable. A patient window 1614 displays patient information, such as name, age, eye condition, etc. An OSDI window displays the patient's OSDI score. Two image windows 1621, 1622 display images of the left eye and right eye, respectively. A first title window 1630 displays title "NiBUT" since the window 1631 immediately below displays NiBUT results. Two image windows 1632, 1633 display a ring pattern projection image and a corresponding ring pattern distortion heatmap for the left eye and right eye, respectively. Two additional image windows 1634, 1635 display eye blink monitoring diagrams drawn from ring pattern projection videos for the left eye and right eye, respectively. A second title window 1640 displays the title "Iris and Meniscus Measures" since the window 1641 immediately below displays iris interferometric pattern and meniscus measurement results. Two image windows 1642, 1643 display tear meniscus images with text indicating measured meniscus heights for the left eye and right eye, respectively. Two additional image windows 1644, 1645 display iris interferometric pattern images for the left eye and right eye, respectively. Two final image windows 1646, 1647 display eye blink monitoring diagrams for the left eye and right eye, respectively. A text field 1650 displays explanatory information based on the displayed eye scan results.

Some portions of this specification are presented in terms of algorithms or symbolic representations of operations on data stored as bits or binary digital signals within a machine memory (e.g., a computer memory). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve the manipulation of information elements. Typically, but not necessarily, such elements may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," "words," "materials," etc. These specific words, however, are merely convenient labels and are to be associated with appropriate information elements.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

Upon reading this disclosure, those of skill in the art will appreciate still additional alternative structural and functional designs for a system and a process for cognitive training through the disclosed principles herein. Thus, while particular embodiments and applications have been illustrated and described, it is to be understood that the disclosed embodiments are not limited to the precise construction and components disclosed herein. Various modifications, changes, and variations, which will be apparent to those skilled in the art, may be made in the arrangement, operation and details of the method and apparatus disclosed herein without departing from the spirit and scope of the invention.

It will also be understood by those familiar with the art, that the invention may be embodied in other specific forms without departing from the spirit or essential characteristics thereof. Likewise, the particular naming and division of the modules, managers, functions, systems, engines, layers, features, attributes, methodologies, and other aspects are not mandatory or significant, and the mechanisms that implement the invention or its features may have different names, divisions, and/or formats. Furthermore, as will be apparent to one of ordinary skill in the relevant art, the modules, managers, functions, systems, engines, layers, features, attributes, methodologies, and other aspects of the invention can be implemented as software, hardware, firmware, or any combination of the three. Of course, wherever a component of the present invention is implemented as software, the component can be implemented as a script, as a standalone program, as part of a larger program, as a plurality of separate scripts and/or programs, as a statically or dynamically linked library, as a kernel loadable module, as a device driver, and/or in every and any other way known now or in the future to those of skill in the art of computer programming. Additionally, the present invention is in no way limited to implementation in any specific programming language, or for any specific operating system or environment.

While this invention has been described in terms of several embodiments, there are alterations, modifications, permutations, and substitute equivalents, which fall within the scope of this invention. Although subsection titles have been provided to aid in the description of the invention, these titles are merely illustrative and are not intended to limit the scope of the present invention. In addition, where claim limitations have been identified, for example, by a numeral or letter, they are not intended to imply any specific sequence.

This has been a description of the disclosed invention along with a preferred method of practicing the invention.

What is claimed is:

1. A system for treatment of dry eye syndrome, comprising:

a projector, including a projector cone and a light source, the projector configured to project a ring pattern onto an anterior surface of an eye wherein the projector includes a lens system configured to focus into a camera an image of the anterior surface;

an eye cup configure to align the camera with the eye;

a machine capable of executing instructions embodied as software; and a plurality of software portions, wherein one of the software portions is configured to capture a video of the anterior surface, identify an iris location, identify a lower tear meniscus location, perform a ring pattern deformation analysis to measure one or more of: a distortion heat map, a tear film breakup time, a tear meniscus height, and an optimal tear meniscus height, segment and analyze the video using the iris location, the lower tear meniscus location, and the ring pattern, recognize a plurality of eye blink events to measure an eye blink rate, compare an image of a corneal lip to an example interferometric pattern to recognize a corneal lip interferometric pattern, and identify one or more parameters indicative of a dry eye condition.

2. The system for treatment of dry eye syndrome of claim 1, wherein the projector includes an eye cup configured to selectively rotate between a first orientation and a second orientation, wherein the first orientation positions the camera to image a right eye, and the second orientation positions the camera to image a left eye.

3. The system for treatment of dry eye syndrome of claim 1, wherein the machine is a mobile computer, and the mobile computer further comprises the camera.

4. The system for treatment of dry eye syndrome of claim 3, further comprising: a docking slot for mechanically interacting with the mobile computer to align the camera and the lens system.

5. A device, comprising:

a projector, including a projector cone and a light source, the projector configured to project a ring pattern onto an anterior surface of an eye;

a lens system configured to focus into a camera an image of the anterior surface of the eye;

an eye cup configured to align the camera and projector with the eye; and a communication system configured to communicate with a mobile compute; and a computer-readable storage medium tangibly embodying a program of instructions executable by the mobile computer wherein said program of instruction comprises a plurality of program codes configured to capture a video of the anterior surface, identify an iris location, identify a lower tear meniscus location perform a ring pattern deformation analysis to measure one or more of: a distortion heat map, a tear film breakup time, a tear meniscus height, and an optimal tear meniscus height, segment and analyze the video using the iris location, the lower tear meniscus location, and the ring pattern, recognize a plurality of eye blink events to measure an eye blink rate, compare an image of a corneal lip to an example interferometric pattern to recognize a corneal lip interferometric pattern, and identify one or more parameters indicative of a dry eye condition.

6. The device of claim 5, wherein the eye cup is configured to selectively rotate between a first orientation and a second orientation, wherein the first orientation positions the camera to image a right eye, and the second orientation positions the camera to image a left eye.

7. The device of claim 5, further comprising: a docking slot for mechanically interacting with the mobile computer, the docking slot configured to align the camera with the projector cone and the lens system, and to removably secure the mobile computer in place.

8. A method of treating dry eye syndrome, comprising:

projecting by a projector aligned over an eye by an eye cup, a ring pattern on to an anterior surface of the eye;

capturing by a camera a video of the anterior surface of the eye;

processing, by a machine capable of executing instructions embodied as software, a plurality of software portions, wherein one of the software portions is configured to identify an iris location, identify a lower tear meniscus location, perform a ring pattern deformation analysis to measure one or more of: a distortion heat map, a tear film breakup time, a tear meniscus height, and an optimal tear meniscus height, segment and analyze the video using the iris location, the lower tear meniscus location, and the ring pattern, recognize a plurality of eye blink events to measure an eye blink rate, compare an image of a corneal lip to an example interferometric pattern to recognize a corneal lip interferometric pattern, and identify one or more parameters indicative of a dry eye condition.

9. The method of treating dry eye syndrome of claim 8, further comprising dividing the ring pattern into a plurality of segments;

constructing a histogram for one or more of the plurality of segments; and calculating a ring pattern distortion value for the one or more of the plurality of segments using the histogram of the one or more of the plurality of segments.

10. The method of treating dry eye syndrome of claim 9, wherein constructing includes weighting the histogram of the one or more of the plurality of segments by multiplying weighting parameters of the histogram of segments adjacent to the one or more of the plurality of segments.

* * * * *